United States Patent [19]
Carter

[11] Patent Number: 5,641,681
[45] Date of Patent: Jun. 24, 1997

[54] DEVICE AND METHOD FOR SCREENING CRYSTALLIZATION CONDITIONS IN SOLUTION CRYSTAL GROWTH

[75] Inventor: Daniel C. Carter, Decatur, Ala.

[73] Assignee: The United States of America as represented by the Administrator of the National Aeronautics and Space Administration, Washington, D.C.

[21] Appl. No.: 422,963

[22] Filed: Apr. 17, 1995

[51] Int. Cl.⁶ .............................. C30B 7/00; G01N 31/00
[52] U.S. Cl. ........................... 436/4; 436/86; 422/245.1; 117/70; 117/201; 117/901
[58] Field of Search ..................... 422/100, 245.1; 436/4, 86; 117/70, 200, 201, 901

[56] References Cited

U.S. PATENT DOCUMENTS

| | | | |
|---|---|---|---|
| 4,791,060 | 12/1988 | Chandler | 422/100 X |
| 4,833,233 | 5/1989 | Carter | 530/363 |
| 4,886,646 | 12/1989 | Carter et al. | 422/245 |
| 4,909,933 | 3/1990 | Carter et al. | 210/95 |
| 4,917,707 | 4/1990 | Claramonte et al. | 117/70 |
| 5,013,531 | 5/1991 | Snyder et al. | 422/245 |
| 5,096,676 | 3/1992 | McPherson et al. | 422/245 |
| 5,130,105 | 7/1992 | Carter et al. | 422/245 |
| 5,419,278 | 5/1995 | Carter | 117/206 |

OTHER PUBLICATIONS

McPherson, "Preparation and Analysis of Protein Crystals," 1982, Chapter 4, pp. 82–127.
Bugg, "The Future of Protein Crystal Growth," Journal of Crystal Growth 76 (1986) pp. 535–544, North–Holland, Amsterdam.
Miller, et al., "A comparison between protein crystals grown with vapor diffusion methods in microgravity and protein crystals using a gel liquid—liquid diffusion ground based method," Journal of Crystal Growth 122 (1992), pp. 306–309, North–Holland, Amsterdam.
Gernert, et al., "A Simple Apparatus for Controlling Nucleation and Size in Protein Crystal Growth," Analytical Biochemistry 168, pp. 141–147 (1988), U.S.A.

M.D. Lind *AIAA* Jan. 1978, 16, 458–462.

D.H. Thomas et al. *Protein Eng.* 1989, 2, 489–491.

J.P. Zeelen et al. *J. Cryst. Growth* 1992, 122, 194–198.

J.M. Garcia–Ruiz et al. *Mat. Res. Bull.* 1993, 28, 541–546.

*Primary Examiner*—Arlen Soderquist
*Attorney, Agent, or Firm*—Brian S. Welborn

[57] ABSTRACT

A device and method for detecting optimum protein crystallization conditions and for growing protein crystals in either 1g or microgravity environments comprising a housing defining at least one pair of chambers for containing crystallization solutions. The housing further defines an orifice therein for providing fluid communication between the chambers. The orifice is adapted to receive a tube which contains a gelling substance for limiting the rate of diffusive mixing of the crystallization solutions. The solutions are diffusively mixed over a period of time defined by the quantity of gelling substance sufficient to achieve equilibration and to substantially reduce density driven convection disturbances therein.

The device further includes endcaps to seal the first and second chambers. One of the endcaps includes a dialysis chamber which contains protein solution in which protein crystals are grown. Once the endcaps are in place, the protein solution is exposed to the crystallization solutions wherein the solubility of the protein solution is reduced at a rate responsive to the rate of diffusive mixing of the crystallization solutions. This allows for a controlled approach to supersaturation and allows for screening of crystal growth conditions at preselected intervals.

40 Claims, 6 Drawing Sheets

☐ — 1% agarose gel, 2mm diameter tube, 22mm length tube

◇ — 1% agarose gel, 4mm diameter tube, 11mm length tube

○ — .6% agarose gel, 4mm diameter tube, 11mm length tube

△ — .6% agarose gel, 4mm diameter tube, 22mm length tube

∗ — .3% agarose gel, 4mm diameter tube, 22mm length tube

DEVICE AND METHOD FOR SCREENING CRYSTALLIZATION CONDITIONS IN SOLUTION CRYSTAL GROWTH

ORIGIN OF THE INVENTION

The present invention was made by an employee of the United States Government and may be manufactured and used by or for the Government for governmental purposes without the payment of any royalties.

FIELD OF THE INVENTION

The present invention relates generally to a device and method for screening optimum crystallization conditions in solution crystal growth and more particularly to a device and method which identifies optimum crystallization conditions while using substantially less protein solution and fewer experiments. In even greater particularity, the present invention relates to a device comprising at least one pair of chambers for containing crystallization solutions connected together by a gel filled channel or tube which limits the rate of diffusive mixing of the crystallization solutions (i.e., a diffusion limited process) thus providing a convenient means for controlling the approach to critical supersaturation in crystal growth and/or screen for possible crystallization conditions.

BACKGROUND OF THE INVENTION

The determination of the three dimensional atomic structure of matter is one of the most important areas of pure and applied research. This field, known as X-ray crystallography, utilizes the diffraction of X-rays from crystals in order to determine the precise arrangement of atoms within the crystal. The result may reveal the atomic structure of substances as varied as metal alloys to the structure of deoxyribonucleic acid (DNA). Some of the greatest discoveries in the history of science have been made by crystallographers. The limiting step in all of these areas of research involves the growth of a suitable crystalline sample.

One important and rapidly growing field of crystallography is protein crystallography. Proteins are polymers of amino acids and contain thousands of atoms in each molecule. Considering that there are 20 essential amino acids in nature, one can see that there exist virtually an inexhaustable number of combinations of amino acids to form protein molecules. Inherent in the amino acid sequence or primary structure is the information necessary to predict the three dimensional structure. Unfortunately, science has not yet progressed to the level where this information can be obtained apriori. Although considerable advances are being made in the area of high field nuclear magnetic resonance, at the present time, the only method capable of producing a highly accurate three dimensional structure of a protein is by the application of X-ray crystallography. This requires the growth of reasonably ordered protein crystals (crystals which diffract X-rays to at least 3.0 angstroms resolution or less).

Because of the complexity of proteins, obtaining suitable crystals can be quite difficult. Typically several hundred to several thousand individual experiments must be performed to determine crystallization conditions, each examining a matrix of pH, buffer type, precipitant type, protein concentration, temperature, etc. This process is extremely time consuming and labor intensive. In this regard, the field is often considered more of an art than a science and skilled practitioners are highly valued. The resulting three dimensional structure produced from the protein crystals can have enormous implications in the fundamental understanding of molecular biology such as how enzymes perform various catalytic activities, switch on biological pathways, or transport molecules within the circulatory system. In the past few years the determination of protein structures important as therapeutic targets has made possible the rational design of new more effective pharmaceuticals.

Recent advances in this field such as high speed computer graphics and X-ray area detection technologies has revolutionized the pace at which the three-dimensional structures can be determined. Still, however, the bottle neck has been the determination of conditions necessary to grow high quality protein crystals. In order for protein crystals to be suitable for structural analysis via X-ray diffraction methods, crystals on the order of about 0.5 mm in diameter or greater must be obtained depending on the intrinsic quality of the protein crystal, the size of the unit cell, and the flux of the X-ray source, etc. This has proved extremely inconvenient and difficult to accomplish on a consistent basis using techniques and crystallization trays known at present.

At present, proteins and other small molecules are crystallized by a variety of conventional experimental methods. Among these many methods, there are three that are most commonly used in the art. One of the main techniques available for growing crystals, known as the hanging-drop or vapor diffusion method, is a method wherein a drop of a solution containing protein is applied to a glass cover slip and placed upside down in an apparatus such as a vapor diffusion chamber where conditions lead to supersaturation in the protein drop and the initiation of precipitation of the protein crystal. However, this method is usually troublesome and inefficient because current methods of employing this technique to achieve crystal growth are somewhat primitive, whether conducted manually or through robotic devices, and involve a series of adjustments of the conditions until a suitable experimental regimen is found. In typical screening methods under this process, it is generally required that the lab technician vary the conditions of pH, buffer type, temperature, protein concentration, precipitant type, precipitant concentration, etc., for each set of experiments, and even adjusting for the myriad of conditions, often only minute samples of the protein can be studied at one time. These variables create an extensive and complex matrix of small experiments, with each series requiring another set of protein drops to be affixed to the glass cover slips and inverted and sealed in the vapor pressure chamber. As presently carried out using currently available devices, crystal growth methods such as the hanging drop method are tedious, time-consuming, and hard to carry out successfully and efficiently with reproducibility.

In another method referred to as the dialysis method, the protein solution is contained within a semipermeable size exclusion membrane and then placed in a solution of fixed pH, precipitant concentration, etc., as in the reservoir solutions prepared for the hanging-drop method. As the precipitant diffuses through the membrane into the protein compartment, the solubility of the protein is reduced and crystals may form. Both vapor diffusion and dialysis methods require extensive screening of numerous variables to achieve the desired results.

Unfortunately, it has been observed that crystal growth carried out under normal gravitational conditions suffer from turbulent convective flows which occur in the above described methods. In particular, during crystal growth under 1 g, the solute depleted regions surrounding a growing crystal normally produce these turbulent convective flows which appear to have significant effects on the crystal quality. For methods such as liquid—liquid diffusion and dialysis, which require the diffusive mixing of two solutions of greatly differing densities, the elimination or reduction of these density driven convective flows is of the utmost importance if one is to successfully carry out crystal growth.

Still another method of protein crystal growth involves what is referred to as gel crystal growth. This method involves the placement of a gel into the end of small diameter glass capillaries. After the solutions have gelled, a protein solution is placed into one end (top) of the capillary and the other end is submerged in a solution of precipitating agent. If the conditions are appropriately selected, crystal growth occurs at a point in the gel where the protein and precipitating agent reach the proper concentrations as the solutions slowly mix by diffusion. Since this is a diffusion limited process, it thus only occurs after an extended period of time. Crystals however, grown by this method are often larger and of higher quality. The approach to screening for the proper crystallization conditions entails the use of numerous bottles of precipitant solutions containing glass capillaries. The method is thus cumbersome and has the disadvantage of that once the crystals are formed in the gels it is extremely difficult to remove them without damage.

In short, the currently accepted practice of screening for protein crystallization conditions suffers from a myriad of problems which have limited the use of high resolution x-ray crystallographic methods in the determination of the three dimensional structures of the protein molecules. It is thus highly desirable in light of the recent advances in the field of protein crystallography to develop highly efficient, simple, and effective methodologies for obtaining the desired conditions for the growth of high quality protein crystals for x-ray crystallography, and yet which can also avoid the problems associated with the prior art devices, and in this respect, the present invention addresses this need and interest.

SUMMARY OF THE INVENTION

In view of the foregoing disadvantages in the known devices and methods of screening for protein crystallization conditions now present in the art, the present invention provides a new and improved device and method for growing protein crystals and for screening crystallization conditions in solution crystal growth. As such, the principal object of the present invention, which will be described subsequently in greater detail, is to provide a new and improved device and method for growing protein crystals and for screening crystallization conditions in solution crystal growth which has all the advantages of the prior art and none of the disadvantages.

In support of the principal object, a further object of the present invention is to provide a new and improved device and method for growing protein crystals and for screening crystallization conditions in solution crystal growth which allows for a highly efficient means to screen for optimum protein crystal growth conditions which will allow the growth of protein crystals of sufficient size and quality for application in X-ray crystallography.

It is still further an object of the present invention to provide a new and improved device and method for growing protein crystals and for screening crystallization conditions in solution crystal growth which can utilize a variety of crystal growth methods to produce protein crystals of greater size and quality than those which can be produced using prior art devices.

It is still further an object of the present invention to provide a new and improved device and method for growing protein crystals and for screening crystallization conditions in solution crystal growth which can be used to screen for crystal growth conditions for any variety of small-molecule crystals.

It is yet another object of the present invention to provide a new and improved device and method for growing protein crystals and for screening crystallization conditions in solution crystal growth which greatly reduces the total manpower required for conducting experiments with the present invention.

Still another object of the present invention is to provide a new and improved device and method for growing protein crystals and for screening crystallization conditions in solution crystal growth which will utilize a gelling substance for limiting or controlling the rate of diffusive mixing of crystallization solutions so that the solutions are diffusively mixed over a predetermined period of time sufficient to achieve equilibration and to substantially reduce density driven convection disturbances therein.

A further object of the present invention is to provide a new and improved device and method for growing protein crystals and for screening crystallization conditions in solution crystal growth which substantially eliminates and controls convective flows associated with normal 1 g gravitational conditions thus providing a diffusion limited process.

Another object of the present invention is to provide a new and improved device and method for growing protein crystals and for screening crystallization conditions in solution crystal growth which eliminates numerous experiments to find the appropriate experimental factors for optimum crystal growth thus lending itself to automation.

Still a further object of the present invention is to provide a new and improved device and method for growing protein crystals and for screening crystallization conditions in solution crystal growth which may be used for large scale commercial crystallization screenings and crystal growth.

It is yet another object of the present invention to provide a new and improved device and method for growing protein crystals and for screening crystallization conditions in solution crystal growth which will substantially eliminate human interaction to activate experiments which is especially helpful in space missions.

Another object of the present invention is to provide a new and improved device and method for growing protein crystals and for screening crystallization conditions in solution crystal growth that will indicate precise experimental factors for growing larger and better quality crystals.

A further object of the present invention is to provide a new and improved device and method for growing protein crystals and for screening crystallization conditions in solution crystal growth which allows for easy removal and access of crystals without damage.

Still yet another object of the present invention is to provide a new and improved device and method for growing protein crystals and for screening crystallization conditions in solution crystal growth which substantially decreases the amount of expensive protein solution required for experiments.

Another object of the present invention is to provide a new and improved device and method for growing protein crystals and for screening crystallization conditions in solution crystal growth which is easily mass produced and prepackaged, thus less expensive to manufacture.

A further object of the present invention is to provide a new and improved device and method for growing protein crystals and for screening crystallization conditions in solution crystal growth which requires a much lower level of skill to perform experiments.

These together with other objects of the present invention, along with the various features of novelty which characterizes the invention, are accomplished through the use of a device and method for growing protein crystals and for screening crystallization conditions in solution crystal growth which comprises a housing having at least one pair chambers for containing crystallization solutions. The chambers each have an opening to the exterior of the housing. The housing further includes a fluid communicating orifice connecting each pair of chambers wherein the orifice is adapted to receive a detachable tube which contains a predetermined quantity of gelling substance for limiting and/or controlling the rate of diffusive mixing of the crystallization solutions. When activated, the solutions are diffusively mixed over a predetermined period of time, defined by the quantity of gelling substance, sufficient to achieve equilibration of the two crystallization solutions and to substantially reduce density driven convection disturbances therein.

The device further includes endcaps for sealingly closing the openings of the two chambers. One of the endcaps includes a dialysis chamber for containing a preselected quantity of protein solution secured by a semipermeable membrane. In another embodiment, the device may use glass coverslips instead of endcaps when performing hanging drop vapor diffusion experiments.

Limiting the rate of diffusive mixing of the two crystallization solutions enables protein crystals to be grown of sufficient size and quality to withstand crystal structural analysis using x-ray diffraction techniques. In operation, the protein solution is exposed to one of the crystallization solutions wherein the solubility of the protein solution is responsibly reduced at a rate substantially equal to the rate of diffusive mixing of the two crystallization solutions through the gelling substance. This rate controls the approach to supersaturation of the protein solution and allows for quality crystals to be grown. It also allows for screening of crystal growth conditions at preselected intervals and substantially reduces density driven convection within the protein solution.

There has thus been outlined, rather broadly, the more important features of the present invention in order that the detailed description thereof that follows may be better understood, and that the present contribution to the art may better appreciated. There are, of course, numerous other novel features of the present invention that will become apparent from a study of the drawings and the description of the preferred embodiments and which will form the subject matter of the claims appended hereto.

Moreover, it is to be understood that the phraseology and terminology employed herein are for the purpose of description and should not be regarded as limiting. As such, those skilled in the art will appreciate that the conception, upon which this disclosure is based, may readily be utilized as a basis for the designing of other systems for carrying out the several purposes of the present invention. It is important, therefore, that the claims be regarded as including such equivalent systems insofar as they do not depart from the spirit and scope of the present invention.

BRIEF DESCRIPTION OF THE DRAWINGS

The foregoing objects and advantages of the present invention for a new and improved device and method for growing protein crystals and for screening crystallization conditions in solution crystal growth will be more readily understood by one skilled in the art by referring to the following detailed description of the preferred embodiments and to the accompanying drawings which form a part of this disclosure, and wherein.

DETAILED DESCRIPTION OF THE PREFERRED EMBODIMENTS

Figure 1:
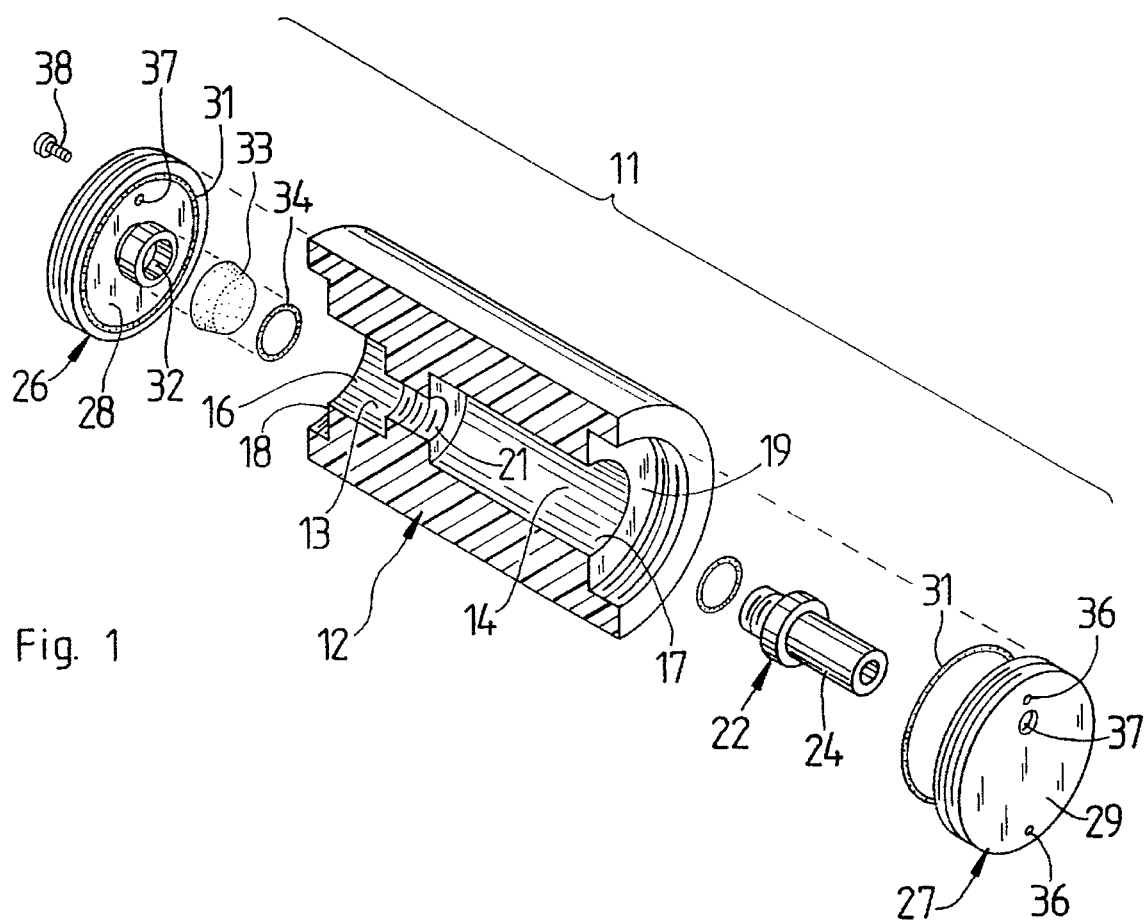
FIG. 1 is an exploded view of a first embodiment of the present invention, showing a housing with a pair of horizontally disposed generally cylindrical chambers therein, two endcaps, and a tube for containing a gelling substance (not shown)

Referring to the drawings for a clearer understanding of the present invention, FIGS. 1–5 disclose a first embodiment of the present invention which comprises a new and improved device 11 for determining optimum crystallization conditions in solution crystal growth and for growing protein crystals of sufficient size and quality to withstand crystal structural analysis using x-ray diffraction techniques. The unique construction of and methodologies employed by the device 11 allow for its utilization in either 1 g or extended microgravity environments and will provide invaluable avenues to the understanding of detailed atomic structure and function of biological macromolecules and other substances.

Figure 2:
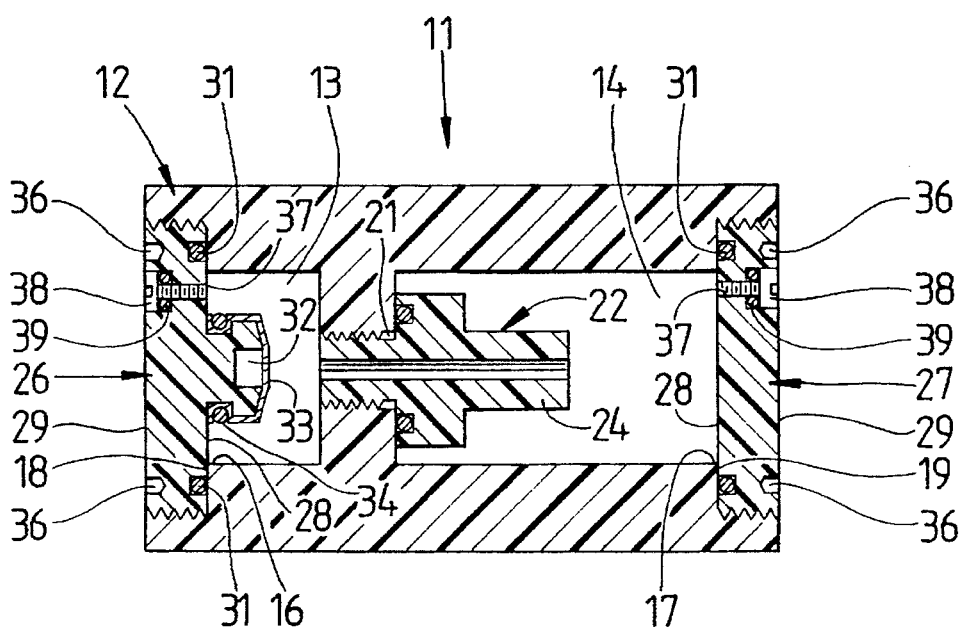
FIG. 2 is a front sectional view of the first embodiment of the present invention, showing the two endcaps and tube positioned within the housing, and further showing a dialysis chamber in one of the endcaps.
Figure 3:
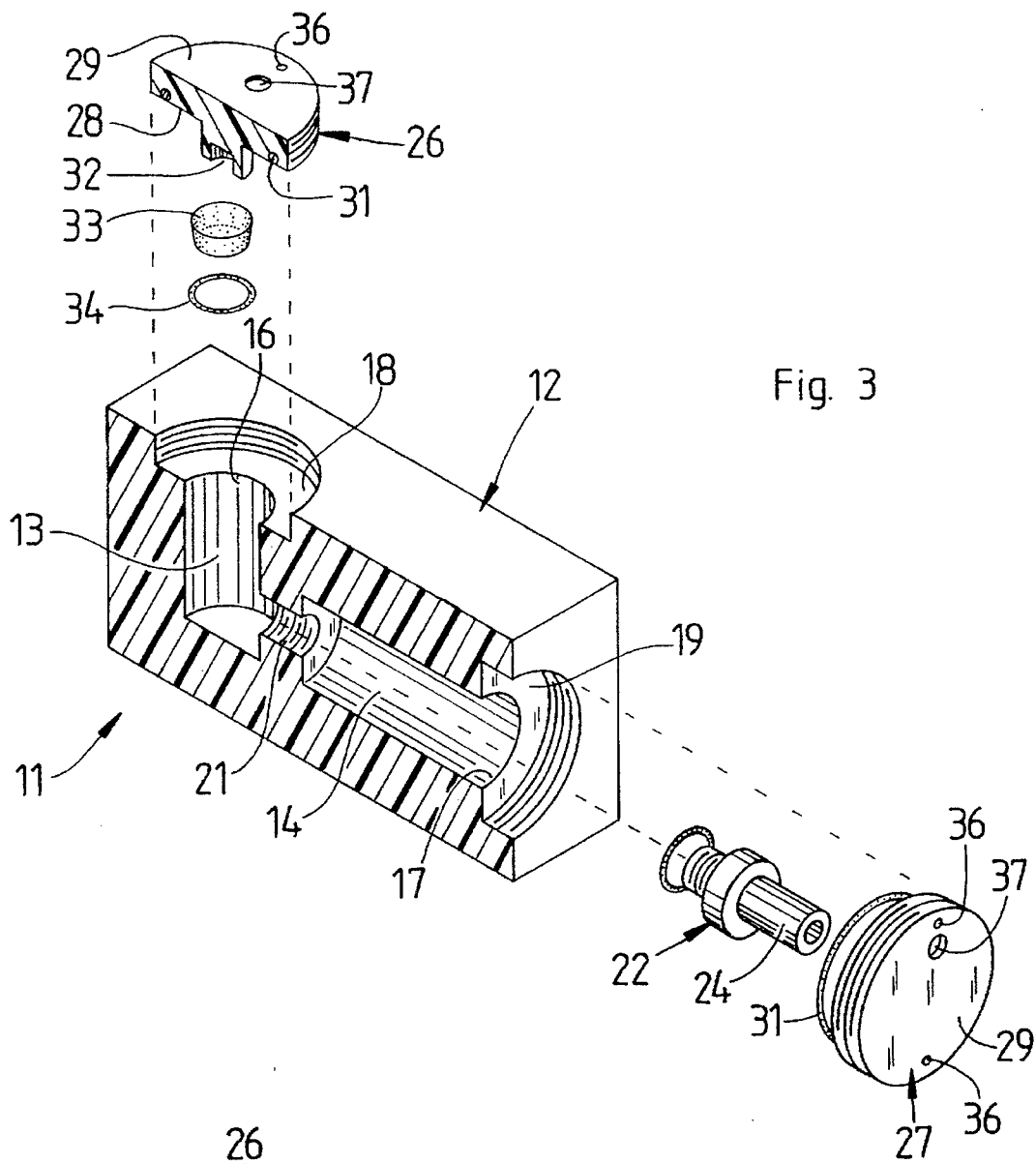
FIG. 3 is a view similar to FIG. 1, but showing a condition wherein one of the chambers is transversely disposed within the housing relative the other chamber.
Figure 4:
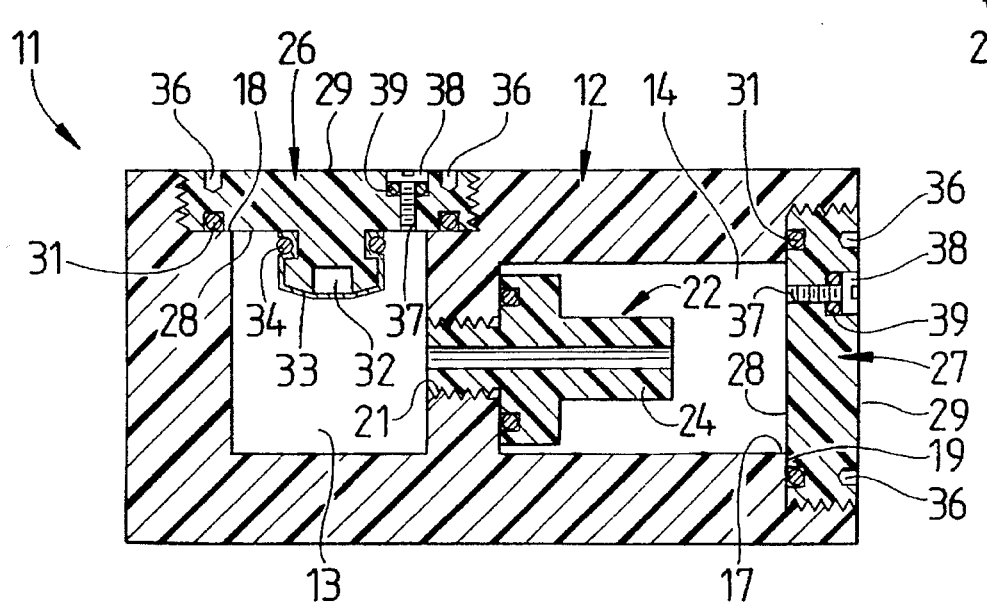
FIG. 4 is a front sectional view of FIG. 3, showing the two endcaps and tube positioned within the housing.
Figure 5:
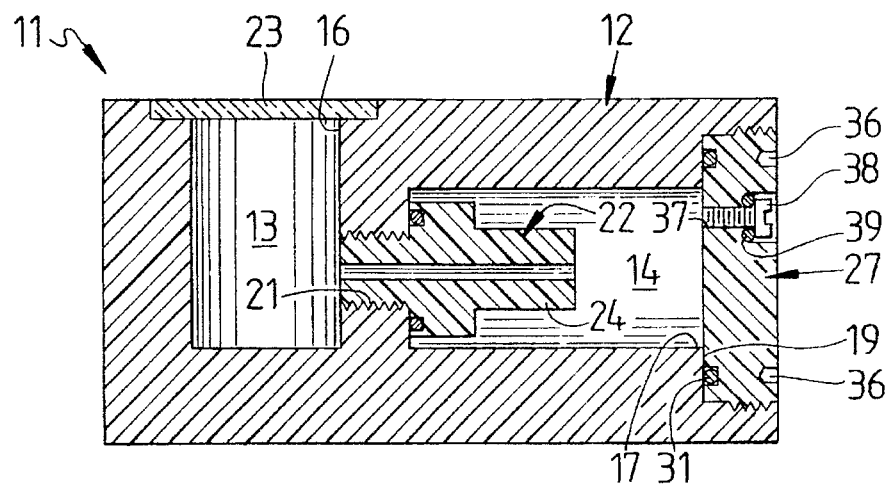
FIG. 5 is a view similar to FIG. 4, but showing a coverslip for one of the chambers instead of an endcap.

Referring to FIGS. 1 and 2, the device 11 may comprise a cylindrical housing 12 having a pair of preferably cylindrical first 13 and second 14 chambers defined therein for containing crystallization (i.e., precursor, precipitant, buffers, etc.) solutions (not shown), respectively. The chambers 13, 14 have first 16 and second 17 openings to the exterior of the housing 12, respectively, for adding and subtracting the crystallization solutions. Even though the housing 12 is preferably cylindrical in shape, it may be rectangular, as shown in FIGS. 3–5, and contain a plurality of pairs of chambers (not shown), preferably up to six pairs, arranged side-by-side. This configuration is most readily employed in commercial bulk crystallizations. Moreover, the housing 12, as disclosed in FIGS. 1–5, has a length of approximately 2.6 inches, and a diameter (height and width) of approximately 1.5 inches. Again, it should be noted that the housing 12 may be any size depending on the circumstances such as in the case of large scale crystallizations.

The device 11 is preferably constructed of transparent plastic such as polystyrene, polycarbonate, polysulphone or high molecular weight polyethylene. Such material allows a user to easily observe crystal growth or crystallization conditions at preselected time intervals during an experiment. However, a variety of other suitable materials could be utilized including glass, as is readily obvious to one skilled in the art.

As noted above, the chambers 13, 14 are preferably cylindrical in shape for ease of construction. Typically, the first chamber 13 is sized to contain approximately 2ml of crystallization solution and the second chamber 14 approximately 6ml, thus having a volume ratio of the first chamber 13 to the second chamber 14 of approximately 1:3. Again, however, the chambers 13, 14 may be considerably larger (i.e., may have any volume ratio) such as in the case of commercial bulk crystallizations.

As illustrated in FIGS. 1 and 2, the first 13 and second 14 chambers are both horizontally disposed and in co-axial alignment within the housing 12. This configuration is typically used in dialysis method experiments. Alternatively, as shown in FIGS. 3–5, the first chamber 13 is transversely disposed (i.e., vertically disposed) relative the second chamber 14 within the housing 12. This configuration is typically used in vapor diffusion method experiments. In both cases or configurations, however, the housing 12 further defines a first annular ledge 18 within the first chamber 13 and a second annular ledge 19 within the second chamber 14.

Furthermore, the housing 12 defines an orifice 21 between the first 13 and second 14 chambers for providing a fluid communication means therebetween. As shown in FIGS. 1 and 2, the orifice 21 is co-axially aligned with both of the chambers 13, 14 and is adapted to detachably receive or threadingly engage a hollow insert or tube 22. The function of the tube 22 is to contain a predetermined quantity of gelling substance (not shown) which acts to limit the rate of diffusive mixing of the first and second crystallization solutions so that the solutions are diffusively mixed over a predetermined period of time sufficient to achieve equilibration and to substantially reduce density driven convection disturbances therein. The tube 22 may be co-extensively positioned or received within the orifice 21 or may have a portion 24 extending a predetermined distance into the second chamber 14 as shown in FIGS. 2, 4 and 5. Thus, the orifice 21 is designed to engage a variety of interchangeable differing diameter and length tubes 22 which will define the quantity of gelling substance contained therein. For non-bulk experiment specific crystallizations, the inner diameter of the tube 22 is approximately 2–4 mm and the length is approximately 11–22 mm.

Referring to FIGS. 1–4, the device 11 further includes first 26 and second 27 endcaps detachably connected to the housing 12 for closing the first 16 and second 17 openings, respectively, of the first 13 and second 14 chambers. Preferably, the endcaps 26, 27 will threadingly engage the housing 12. Each endcap 26, 27 has an inner surface 28 and an outer surface 29 wherein the inner surface 28 engages the first 18 and second 19 annular ledges, respectively, when the endcaps 26, 27 are connected to the housing 12. Moreover, each endcap 26, 27 includes an o-ring 31 for sealingly engaging the first 18 and second 19 annular ledges, respectively.

Alternatively, acrylic tape (not shown) could be used in place of the endcaps 26, 27 such as when commercially available dialysis buttons or bags are placed in the first chamber As noted earlier, the device 11 may be utilized with both dialysis and vapor diffusion method experiments. For dialysis method experiments, as shown in FIGS. 1–4, the first endcap 26 will include a dialysis chamber 32 integrally connected at the center of the inner surface 28 of the first endcap 26 for containing a preselected quantity of protein solution (not shown). The protein solution is contained within the dialysis chamber 32 by use of a semipermeable membrane 33 which is held in place by an o-ring 34. Once the first endcap 26 is connected to the housing 12, the dialysis chamber 32 will be in communication with the first chamber 13, thus exposed to the crystallization solution therein. More specifically, the dialysis chamber 32 will be submerged in the crystallization solution within the first chamber 13.

In both dialysis and vapor diffusion method experiments, the protein solution is exposed to the first crystallization solution wherein the solubility of the protein solution is reduced at a rate responsive or generally equal to the rate of diffusive mixing of the first and second crystallization solutions. This provides a controlled approach to supersaturation of the crystallization solutions and provides an opportunity to screen crystal growth conditions at preselected intervals during the diffusive mixing. It also substantially reduces density driven convection disturbances.

In addition, each endcap 26, 27 defines a pair of pin holes 36 symetrically disposed around the center of the outer surface 29 of the endcaps 26, 27 for mating with a tool to aid in the tightening and removing of the endcaps 26, 27 and for not obstructing a clear viewing of the dialysis chamber 32. Moreover, each endcap 26, 27 defines a vent hole 37 therethrough which is in communication with the first 13 and second 14 chambers. The vent hole 37 includes a standard bolt 38 and o-ring 39 for selectively venting pressure build-up within the chambers 13, 14 during engagement of the endcaps 26, 27.

Referring to FIG. 5, a glass coverslip 23 may be used in place of the first endcap 26. The coverslip 23 is most readily used in "hanging-drop" vapor diffusion method experiments. Acrylic tape (not shown) is used to secure the coverslip 23 to the housing 12. This orientation provides a more convenient means to observe changes via microscopic examination in the protein solution. When the hanging drop method is employed, fluid levels are adjusted to be of equal height in the first 13 and second 14 chambers so that no hydrostatic pressure difference is generated and so that an appropriate volume of vapor phase exists between the protein droplet and the crystallization solution.

In operation, crystal growth and crystallization screens are conducted in the following manner. A suitable gelling substance (not shown) such as polyacrylamide, gelatin, agarose, or silica gel is injected by syringe into the tube 22 and allowed to gel, whereupon the tube 22 is threaded into the orifice 21 inside of the housing 12. A portion of the tube 22 extends a predetermined distance into the second chamber 14 in order to keep the convective disturbances associated with the diffusive mixing of the crystallization solutions away from the protein solution. Once a suitable period has passed for gelling to occur, a concentrated solution of precipitant is added to the second chamber 14 (the precipitant reservoir) and sealed with the second endcap 27. Next, the protein solution is placed in the dialysis chamber 32 and secured with the semipermeable membrane 33 and o-ring 34 or placed on the coverslip 23. Once the protein solution is secured, the first chamber 13 is filled with an appropriate dilute solution of precipitant agent and buffer. When the first chamber 13 is sealed with the first endcap 26 or coverslip 23, the crystallization solutions are in fluid communication with one another. At this time, the experiment has been activated and will progress until the two solutions come to equilibrium.

The length of time to reach equilibrium depends on the size or volume of the communication between the first 13 and second 14 chambers (i.e., primarily the length and diameter of the tube 22 which defines the amount of gelling substance), the volumes of the first 13 and second 14 chambers, as well as, temperature, concentrations between the two crystallization solutions, and other factors. Known classical mathematical formula derived to explain diffusive phenomena are used to calculate the equilibrium times and profiles taking into account these variables.

Figure 11:
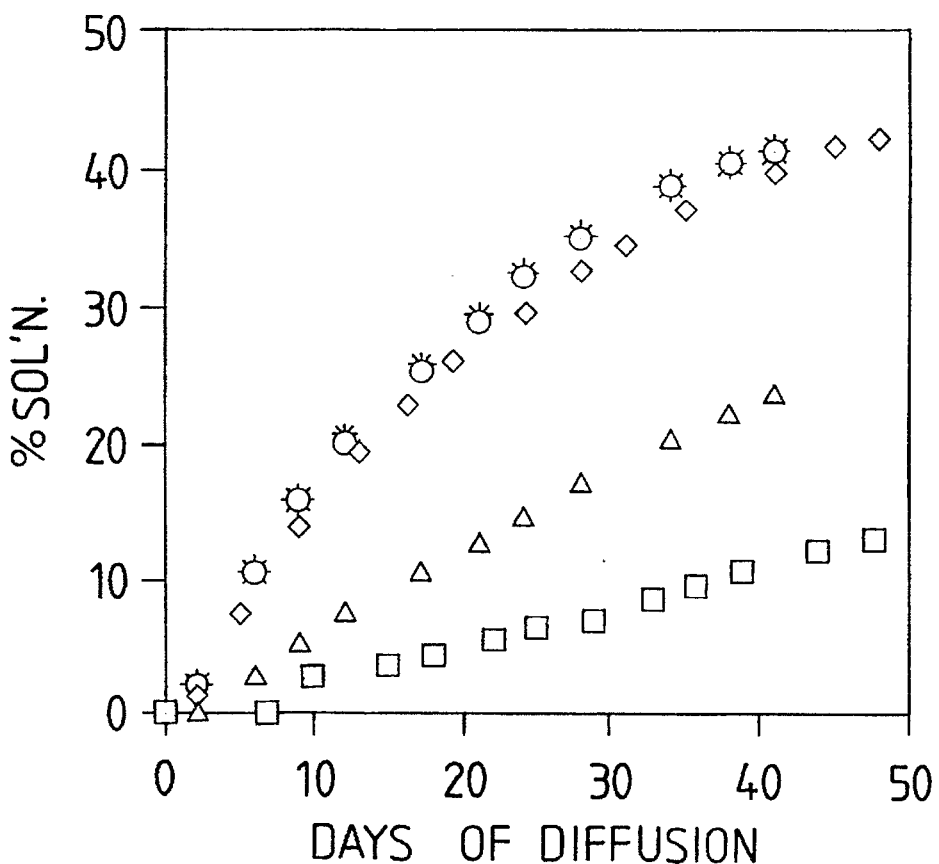
FIG. 11 is a graphical representation of equilibration profiles for identical solutions of saturated ammonium sulphate diffusion rates as a function of tube length, tube inner diameter, and type of gelling substance.

For example, FIG. 11 shows diffusion profiles for identical solutions of saturated ammonium sulphate (SAS) and water through varying concentrations of agarose gel. The water is contained in the first chamber 13 and the ammonium sulphate in the second chamber 14. All five of the diffusion profiles shown were conducted at room temperature. Under typical conditions, the experiments require approximately 3–6 months to reach equilibrium.

As indicated by a "square" in FIG. 11, a tube 22 having an inner diameter of approximately 2 mm and a length of approximately 22 mm which is filled with 1% agarose gel will define a diffusion rate of approximately 1.7% saturated sulphate per week. This means that the concentration of the ammonium sulphate in the water contained in the first chamber 13 will rise at a rate of approximately 1.7% per week until the experiment approaches equilibrium. When the appropriate conditions of supersaturation are met, crystals are induced to form.

As indicated by a "diamond" in FIG. 11, a tube 22 having an inner diameter of approximately 4 mm and a length of approximately 11 mm, which is filled with 1% agarose gel, will define a diffusion rate of approximately 4% saturated sulphate per week. This means that the concentration of the ammonium sulphate in the water contained in the first chamber 13 will rise at a rate of approximately 4% per week until the experiment approaches equilibrium.

As indicated by a "circle" in FIG. 11, a tube 22 having an inner diameter of approximately 4 mm and a length of approximately 11 mm, which is filled with 0.6% agarose gel, will define a diffusion rate of approximately 10% per week. This means that the concentration of the ammonium sulphate in the water contained in the first chamber 13 will rise at a rate of approximately 10% per week until the experiment approaches equilibrium.

As indicated by a "triangle" in FIG. 11, a tube 22 having an inner diameter of approximately 4 mm and a length of approximately 22 mm, which is filled with 0.6% agarose gel, will define a diffusion rate of approximately 10% per week. This means that the concentration of the ammonium sulphate in the water contained in the first chamber 13 will rise at a rate of approximately 10% per week until the experiment approaches equilibrium.

As indicated by a "asterisk" in FIG. 11, a tube 22 having an inner diameter of approximately 4 mm and a length of approximately 22 mm, which is filled with 0.3% agarose gel, will define a diffusion rate of approximately 10% per week. This means that the concentration of the ammonium sulphate in the water contained in the first chamber 13 will rise at a rate of approximately 10% per week until the experiment approaches equilibrium.

This method, whether dialysis or vapor diffusion, requires the preparation in advance of concentrated stock solutions. Most importantly, however, it does not require the tedious preparation of individual experiments at increments in 5% steps of each of the precipitant concentrations (i.e., conditions). Thus, each experiment using the present invention takes the place of approximately 12 prior art crystallization screens. For instance, a typical crystallization screen using prior art devices and methods of five different precipitating agents would consist of approximately 480 individual experiments, regardless of whether they are dialysis or vapor diffusion experiments. In contrast, the same experiment using the present invention would create only 40 experiments and require a much lower skill level to prepare, thus resulting in a considerable savings in time and valuable protein solution.

The experiments are monitored visually on intervals of approximately once a week in order that the proper conditions for crystal growth can be identified. This information may be ascertained in two simple ways: (1) by directly measuring the refractive index of the solution in the first chamber 13; or (2) by noting precisely when crystal growth occurred, such as by automated processes which can be monitored by robotics followed by subsequent calculations of the concentration. Generally, such a slow approach to supersaturation has other advantages as well as that it produces fewer and larger protein crystals of higher quality and that the present invention possesses no moving fluids.

Figure 6:
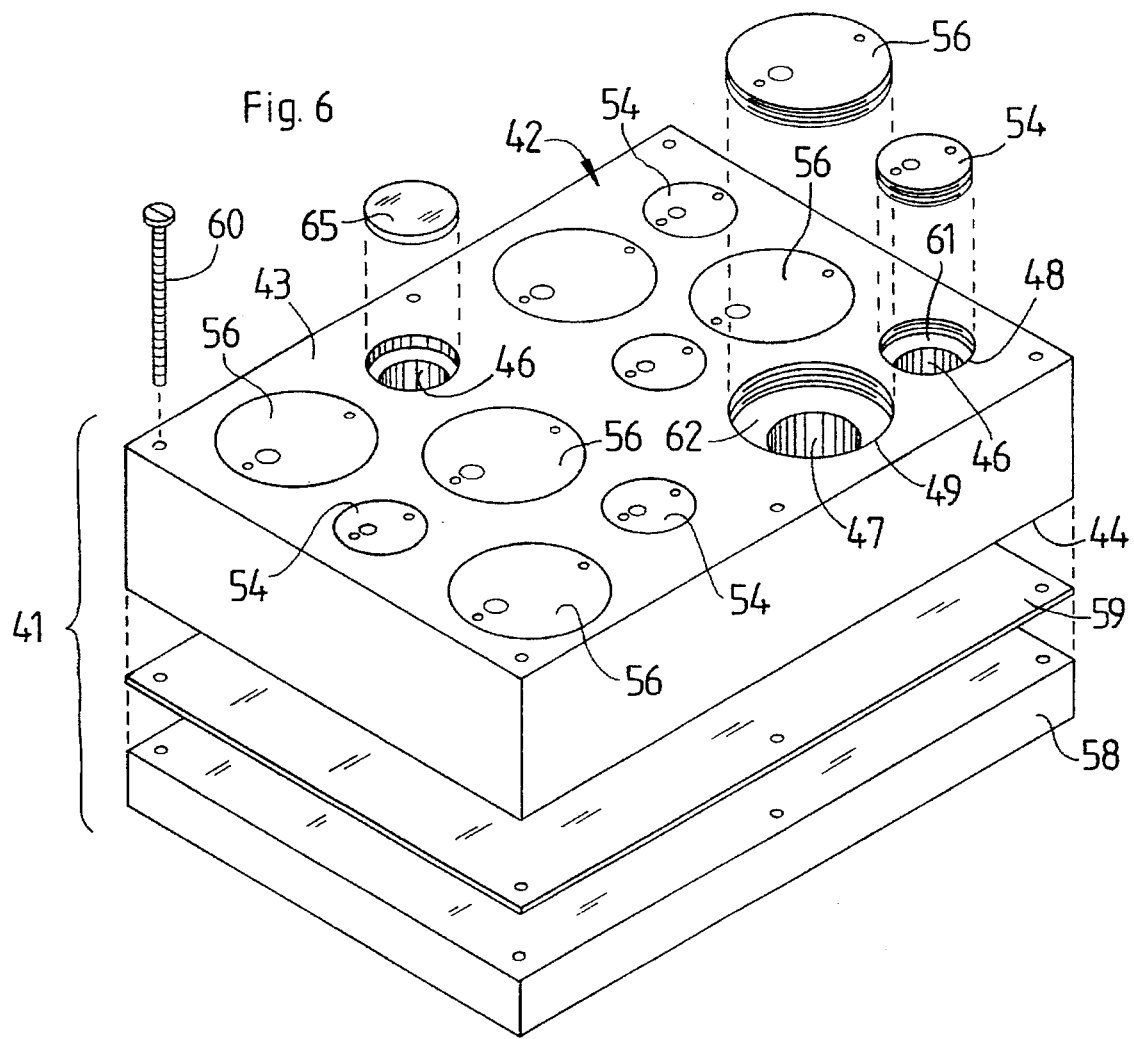
FIG. 6 is an exploded view of a second embodiment of the present invention, showing a tray having a plurality of pairs of vertically disposed chambers, an elastomer sheet, and a bottom plate.
Figure 7:
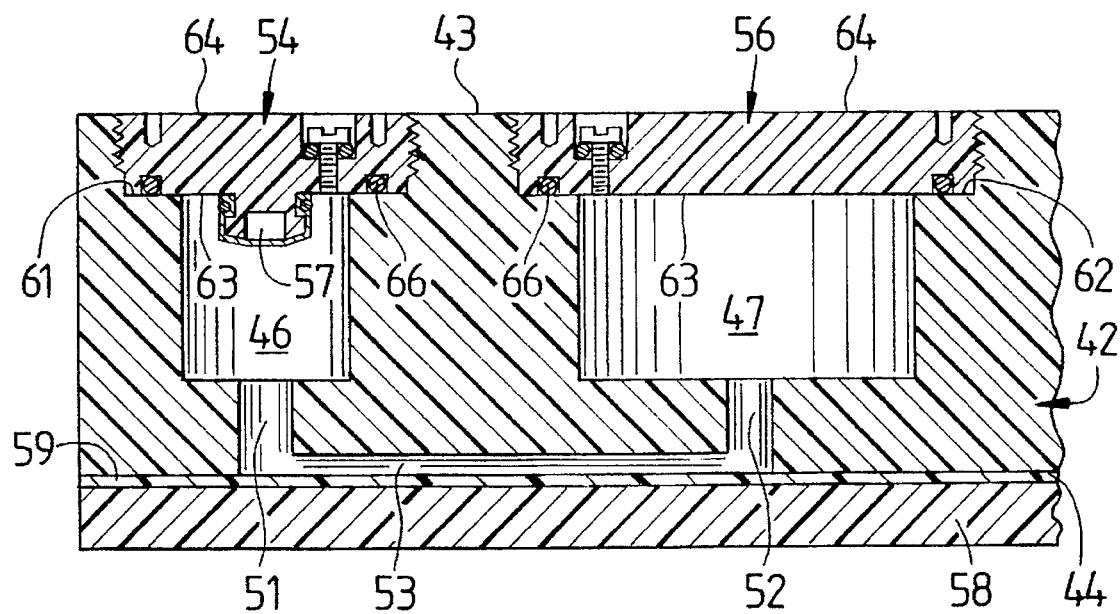
FIG. 7 is a front sectional view of the tray of the second embodiment of the present invention, showing one of the plurality pairs of chambers, two endcaps with one of the endcaps having a dialysis chamber, and a channel defined in a lower surface of the tray for containing a gelling substance (not shown)
Figure 8:
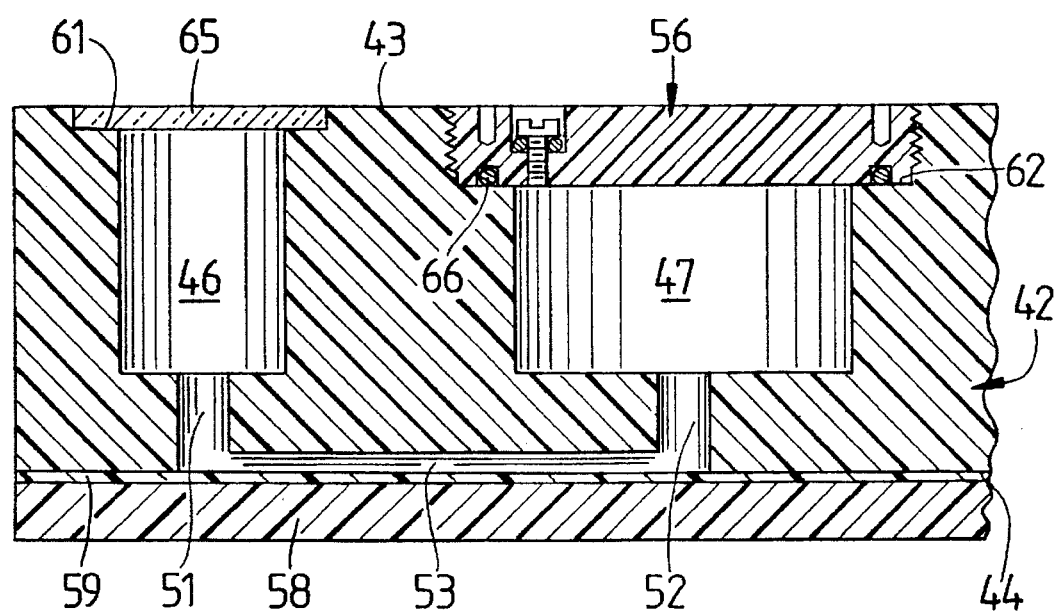
FIG. 8 is a view similar to FIG. 7, but showing a coverslip for one of the chambers instead of an endcap.

A second embodiment of the present invention is illustrated in FIGS. 6–8 which comprises an apparatus 41 for determining optimum protein crystal growth conditions and for growing protein crystals in either 1 g or microgravity environments. The apparatus 41 comprises a preferably rectangular tray 42 having an upper 43 and lower 44 surface. The tray 42 defines at least one pair of first 46 and second 47 vertically disposed chambers therein for containing first and second crystallization solutions, respectively. The chambers 46, 47 are the same size and shape as that described in the first embodiment. Preferably, the tray 42 will include six pairs of chambers 46, 47. The chambers 46, 47 have first 48 and second 49 openings through the upper surface 43 to the exterior of the tray 42, respectively, and first 51 and second 52 orifices through the lower surface 44 to the exterior of the tray 42, respectively.

As shown in FIGS. 7 and 8, the tray 42 further defines a channel 53 in its lower surface 44 which provides continuous fluid communication between the first 51 and second 52 orifices. The channel 53 is adapted to contain a predetermined quantity of gelling substance (not shown) which acts to limit the rate of diffusive mixing of the first and second crystallization solutions wherein the solutions are diffusively mixed over a predetermined period of time defined by the quantity of gelling substance sufficient to achieve equilibration and to substantially reduce density driven convection disturbances therein. Preferably, the channel 53 has a length of approximately 11–22 mm and a width and depth of approximately 2–4 mm.

The apparatus 41 further comprises first 54 and second 56 endcaps detachably connected to the tray 42 for closing the first 48 and second 49 openings, respectively, and are substantially identical to those described in the first embodiment. The first endcap 54 includes a dialysis chamber 57 integrally formed thereto for containing a preselected quantity of protein solution (not shown) in which protein crystals are grown of sufficient size and quality to withstand crystal structural analysis using x-ray diffraction techniques. The protein solution is exposed to the first crystallization solution in the first chamber 46 wherein the solubility of the protein solution is reduced at a rate responsive to the rate of diffusive mixing of the first and second crystallization solutions thus providing a controlled approach to critical supersaturation. This controlled approach allows for screening of crystal growth conditions at preselected intervals during the time of diffusive mixing of the crystallization solutions. Moreover, the controlled approach to supersaturation substantially reduces density driven convection within the protein solution.

As illustrated in FIGS. 6–8, the apparatus 41 further comprises a bottom plate 58 attached to the lower surface 44 of the tray 42 and an elastomer sheet 59 attached intermediate the tray 42 and the bottom plate 58 for sealingly engaging the channel 53 and the first 51 and second 52 orifices. Moreover, the bottom plate 58 and the elastomer sheet 59 are preferably coextensive with the tray 42 (i.e., the same length and width) and connected thereto with machine screws 60 or any other known method.

Again, the first 46 and second 47 chambers are the same shape and volume as those disclosed in the first embodiment of the present invention. Likewise, the tray 42 further defines a first 61 and second 62 annular ledge within the first 46 and second 47 chambers, respectively, proximal the upper surface 43. Each endcap 54, 56 has an inner surface 63 and an outer surface 64 wherein the inner surface 63 engages the first 61 and second 62 annular ledges, respectively, when the endcaps 54, 56 are connected (preferably threaded) to the tray 42. Moreover, each endcap 54, 56 includes an o-ring 66 for sealingly engaging the first 61 and second 62 annular ledges, respectively. As mentioned in the first embodiment, acrylic tape (not shown) could be used in place of the endcaps 54, 56 when commercially available dialysis buttons or bags are placed in the first chamber 46.

Referring to FIG. 8, a glass coverslip 65 may be used in place of the first endcap 54. The coverslip 65 is most readily used in "hanging drop" vapor diffusion method experiments. Acrylic tape (not shown) is used to secure the coverslip 65 to the tray 42.

The method of operation of the second embodiment is a combination of the methods described in the first and third embodiments, thus are incorporated here for convenience. Likewise, the materials used for the elements in the second embodiment are the same as those disclosed in the first embodiment.

Figure 9:
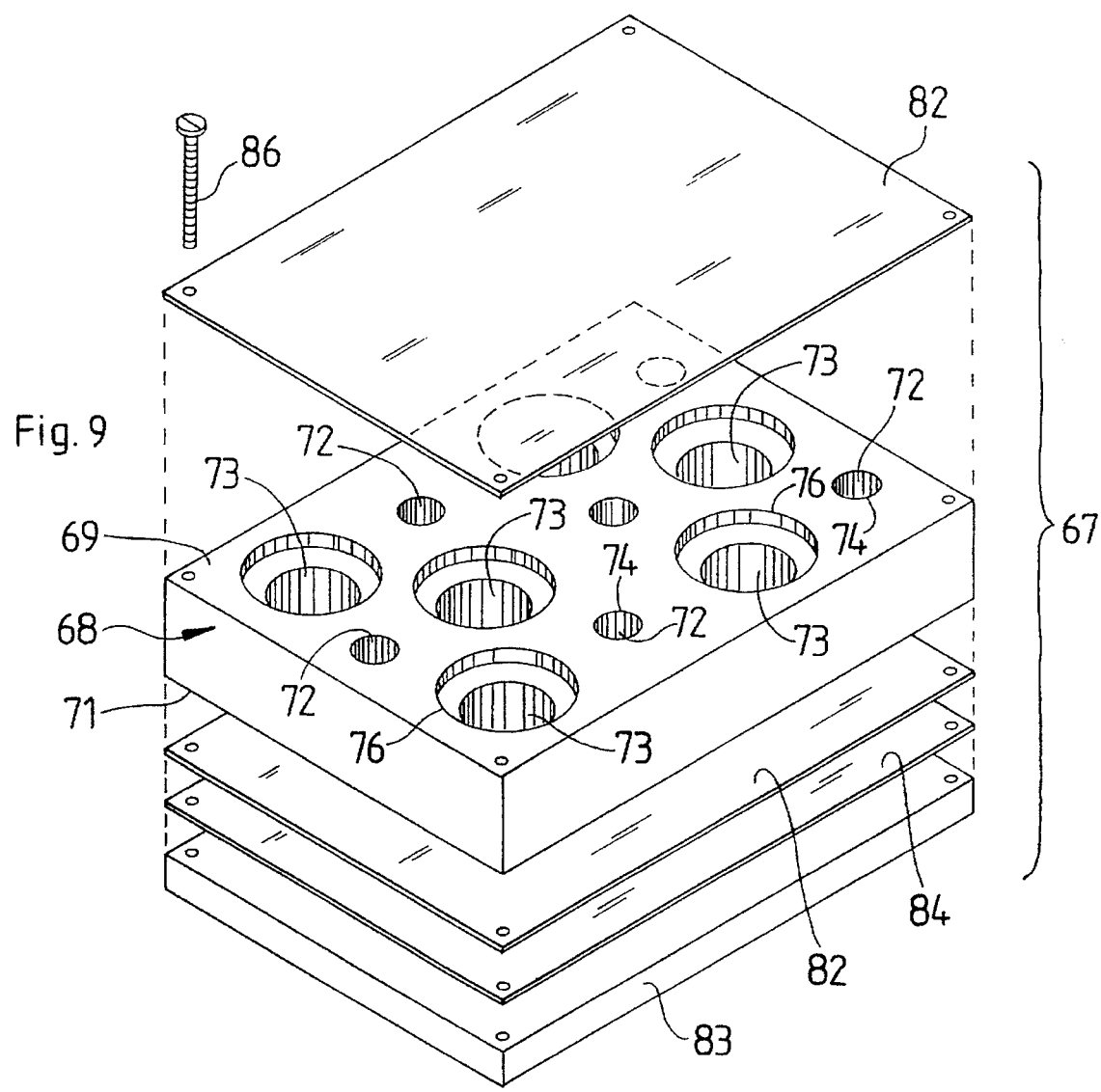
FIG. 9 is an exploded view of a third embodiment of the present invention, showing a tray having an upper and lower surface, a plurality of vertically disposed chambers defined in the tray, a layer of acrylic tape disposed on the upper surface of the tray, a layer of acrylic tape disposed on the lower surface of the tray, an elastomer sheet, and a bottom plate.
Figure 10:
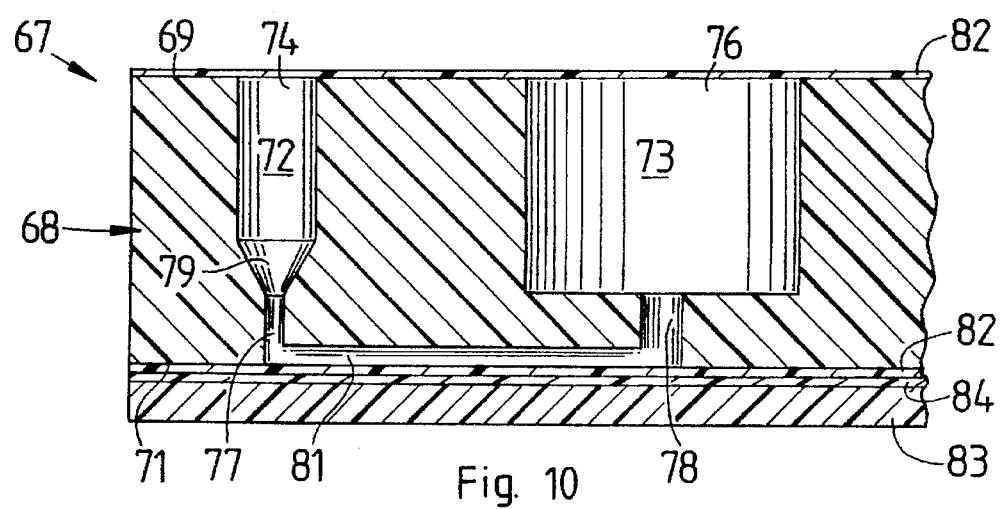
FIG. 10 is a front sectional view of the tray of the third embodiment of the present invention, showing one of the plurality of pairs of vertically disposed chambers, a conically shaped portion of one of the chambers, and a channel for containing a gelling substance (not shown).

A third embodiment of the present invention is shown in FIGS. 9 and 10 which comprises a disposable device 67 for growing easily accessible protein crystals of sufficient size and quality to withstand crystal structural analysis using X-ray diffraction techniques. The device 67 comprises a tray 68 having an upper 69 and lower 71 surface. The tray 68 defines at least one pair of first 72 and second 73 vertically disposed chambers therein for containing a protein solution (not shown) and a precipitant solution (not shown), respectively. As in the second embodiment, the tray 68 will preferably include six pairs of chambers 72, 73, the first chamber 72 however containing approximately ten microliters of protein solution, and the second chamber 73 approximately 500 microliters. Moreover, the tray 68 will have a preferable length of approximately four inches, a width of approximately six inches, and a height of approximately ½ inch.

The chambers 72, 73 further have first 74 and second 76 openings through the upper surface 69 of the tray 68, respectively, and a first restricted orifice 77 and a second orifice 78 through the lower surface 71 of the tray 68, respectively. In addition, the first chamber 72 further defines a conically shaped portion 79 adjacent or proximal to the first restricted orifice 77. The first restricted orifice 77 provides a pressure seal for a syringe (not shown) during injection of a gelling substance, which is described in more detail below.

As shown in FIG. 10, the tray 68 further defines a channel 81 in its lower surface 71 which provides continuous fluid communication between the first 77 and second 78 orifices. The channel 81 is adapted to contain a predetermined quanity of gelling substance (not shown) which limits the rate of diffusive mixing of the protein solution and the precipitant solution wherein the solutions are diffusively mixed over a predetermined period of time defined by the quanity of the gelling substance. It is preferable that the width and depth of the channel 81 be approximately 4 mm and 2 mm, respectively. The time it takes to diffusively mix the solutions should be sufficient to controllably reduce the solubility of the protein solution within the gelling substance to the point of critical supersaturation whereby crystals are induced to grow in the gelling substance within the channel 81.

The device 67 further comprises two layers of clear synthetic plastic tape 82, which can be either polyester or polypropylene, connected to the upper 69 and lower 71 surface of the tray 68 for sealingly engaging the first 74 and second 76 openings and the first 77 and second 78 orifices and channel 81, respectively. The types of tape 82 mentioned above are generally preferred because of their superior sealing and thermal properties and, in addition, employ as an adhesive a compound (acroolefin) which is a safe biocompatible material. Moreover, the device 67 further comprises a bottom plate 83 detachably connected to the lower surface 71 of the tray 68 and an elastomer sheet 84 detachably connected to the lower surface 71 of the tray 68 intermediate the tape 82 on the lower surface 71 and the bottom plate 83.

Preferably, the layers of plastic tape 82, the elastomer sheet 84, and the bottom plate 83, are all coextensive with the tray 68 (i.e., the same rectangular size). In addition, the tray 68 should be constructed out of polystyrene, polycarbonate, polysulphone or high molecular weight polyethylene.

Preferably, the typical operation of the third embodiment would be performed as follows. First, a layer of plastic tape 82 would be attached to the lower surface 71 of the tray 68 to seal the bottom of the tray 68. Then the elastomer sheet 84 and the bottom plate 83 would be connected to the lower surface 71 of the tray 68 covering the plastic tape 82. The elastomer sheet 84 and the bottom plate 83 may either be connected and tightened with machine screws 86 or placed in mechanical press (not shown) suitable for automation purposes so as to compress the elastomer sheet 84 to form an effective seal. The gelling substance (not shown) is then injected by syringe into the channel 81 and allowed to gel.

After gelling has occurred, the device 67 is disassembled leaving the tray 68 with the gelling substance and plastic tape 82 intact. Protein and precipitant solutions (not shown) are then added to the first 72 and second 73 chambers, respectively. Another layer of plastic tape 82 is attached to the upper surface 69 of the tray 68 to seal the upper surface 69. At this time, the experiment has been activated.

Crystals which grow in the gelling substance in the channel 81 are conveniently removed by cutting through the plastic tape 82 and prepared by known methods for X-ray diffraction studies.

The diffusive mixing of the protein and precipitant solutions through a gelling substance described in the above method is accomplished over a period of time defined by the quantity of gelling substance. In light of the dimensions of the channel 81 set out above, which dictate the quantity of gelling substance, the period of time is sufficient to controllably reduce the solubility of the protein solution to the point of supersaturation whereby protein crystals are grown having superior size and quality.

Thus, the device 67 provides a means to produce preprepared disposable gel crystallization trays 68 which can be created inexpensively and which provide a variety of gel options as well as a more convenient method to conduct, store, monitor, and document gel protein crystal growth experiments.

In light of the disclosure of the present invention as set forth above, it is clear that numerous other objects and features of the present invention that are inherent in the disclosure will be readily appreciated by those skilled in the art. For instance, any of the above mentioned embodiments can be easily adapted for utilization in producing crystals in the environment of an orbiting spacecraft having the advantage that the experiments, when prepared prior to launch, do not require human intervention to activate. In addition, it will be well recognized to one skilled in the art that numerous changes and modifications not specifically set forth can be made with regard to the embodiments described above without departing from the scope of the invention which is defined in the claims appended hereto.

What is claimed is:

1. A device for detecting optimum protein crystallization conditions and for growing protein crystals in either 1 g or microgravity environments, said device comprising:

(a) a housing defining a pair of first and second chambers having first and second openings to the exterior of said housing, respectively, for containing first and second crystallization solutions, respectively; said second chamber having a volume at least three times the volume of the first chamber; said housing having a threaded opening extending from the second chamber to the first chamber:

(b) a threaded tube threaded into said threaded opening for containing fluid communication means having means for limiting the rate of diffusive mixing of said first and second crystallization solutions so that said solutions are diffusively mixed over a predetermined period of time sufficient to achieve equilibrium and to substantially reduce density driven convection disturbances therein; and (c) first and second closure means detachably connected to said housing for closing said first and second openings, respectively, said first closure means including crystal growth means in communication with the first chamber through a semipermeable membrane for containing a preselected quantity of protein solution in which protein crystals are grown of sufficient size and quality to withstand crystal structural analysis using x-ray diffraction techniques, said protein solution exposed to said first crystallization solution in said first chamber wherein the solubility of said protein solution is reduced at a rate responsive to said rate of diffusive mixing of said first and second crystallization solutions thus providing a controlled approach to critical supersaturating, said controlled approach allowing for screening of crystal growth at preselected intervals during said period of time and substantially reducing density driven convection therein; said first and second closure means each having a threaded vent hole sealed with a threaded bolt for filling and releasing bubbles from said chambers.

2. A device as defined in claim 1 wherein said tube has a predetermined inner diameter and length and said rate limiting means comprises a predetermined quantity of gelling substance, said predetermined quantity of gelling substance defining said period of time sufficient to achieve equilibration and to substantially reduce density driven convection disturbances within said first and second crystallization solutions.

3. A device as defined in claim 2 wherein a portion of said tube extends a predetermined distance into said second chamber.

4. A device as defined in claim 3 wherein said inner diameter and length of said tube is approximately four millimeters and twenty-two millimeters, respectively.

5. A device as defined in claim 2 wherein said first and second chambers are both generally cylindrical in shape.

6. A device as defined in claim 5 wherein said first and second chambers are both horizontally disposed within said housing.

7. A device as defined in claim 6 wherein said first and second chambers are co-axially aligned within said housing.

8. A device as defined in claim 7 wherein said fluid communication means is co-axially aligned with said first and second chambers in said housing.

9. A device as defined in claim 1 wherein said first closure means comprises a first endcap for detachably engaging said first chamber at said first opening in said housing.

10. A device as defined in claim 9 wherein said housing further defines a first annular ledge within said first chamber for abuttingly engaging said first endcap.

11. A device as defined in claims 10 wherein said first endcap further comprises an o-ring for sealingly engaging said first annular ledge.

12. A device as defined in claim 9 wherein said crystal growth means comprises a dialysis chamber defined in said first endcap and in communication with said first chamber for containing said preselected quantity of protein solution.

13. A device as defined in claim 1 wherein said second closure means comprises a second endcap for detachably engaging said second chamber at said second opening in said housing.

14. A device as defined in claim 13 wherein said housing further defines a second annular ledge within said second chamber proximal said upper surface for engaging said second endcap.

15. A device as defined in claim 14 wherein said second endcap further comprises an o-ring for sealingly engaging said second annular ledge.

16. A device as defined in claim 15 wherein said second chamber is horizontally disposed within said housing.

17. A device as defined in claim 16 wherein said first chamber is transversely disposed relative said second chamber within said housing.

18. A device as defined in claim 17 wherein said housing further defines a first annular ledge within said first chamber.

19. An apparatus for determining optimum protein crystal growth conditions and for growing protein crystals in either 1 g or microgravity environments, said apparatus comprising:

(a) a tray having an upper and lower surface, said tray defining at least one pair of first and second vertically disposed chambers therein for containing first and second crystallization solutions, respectively, said chambers having first and second openings through said upper surface to the exterior of said tray, respectively, and first and second orifices through said lower surface to the exterior of said tray, respectively;

(b) said tray further defining a channel in said lower surface and in communication with said first and second orifices for containing a predetermined quantity of gelling substance which limits the rate of diffusive mixing of said first and second crystallization solutions so that said solutions are diffusively mixed over a predetermined period of time sufficient to achieve equilibration and to substantially reduce density driven convection disturbances therein; and (c) first and second closure means detachably connected to said tray for closing said first and second openings, respectively, said first closure means including crystal growth means in communication with said first chamber for containing a preselected quantity of protein solution in which protein crystals are grown of sufficient size and quality to withstand crystal structural analysis using x-ray diffraction techniques, said protein solution exposed to said first crystallization solution in said first chamber wherein the solubility of said protein solution is reduced at a rate responsive to said rate of diffusive mixing of said first and second crystallization solutions thus providing a controlled approach to critical supersaturation, said controlled approach allowing for screening of crystal growth conditions at preselected intervals during said period of time and substantially reducing density driven convection therein.

20. An apparatus as defined in claim 19 wherein said apparatus further comprises:

(a) a bottom plate attached to said lower surface of said tray; and (b) sealing means connected intermediate said tray and said bottom plate for sealingly engaging said channel.

21. An apparatus as defined in claim 20 wherein said sealing means comprises an elastomer sheet.

22. An apparatus as defined in claim 21 wherein said first and second chambers have a volume ratio of said first chamber to said second chamber of approximately 1:3.

23. An apparatus as defined in claim 22 wherein said first and second chambers are both generally cylindrical in shape.

24. An apparatus as defined in claim 21 wherein said elastomer sheet is coextensive with said tray.

25. An apparatus as defined in claim 21 wherein said first closure means comprises a first endcap for engaging said first chamber at said first opening in said tray.

26. An apparatus as defined in claim 25 wherein said tray further defines a first annular ledge within said first chamber proximal said upper surface for engaging said first endcap.

27. An apparatus as defined in claim 26 wherein said first endcap further comprises an o-ring for sealingly engaging said first annular ledge.

28. An apparatus as defined in claim 27 wherein said crystal growth means comprises a dialysis chamber defined in said first endcap and in communication with said first chamber for containing said preselected quantity of protein solution.

29. An apparatus as defined in claim 21 wherein said second closure means comprises a second endcap for engaging said second chamber at said second opening in said tray.

30. An apparatus as defined in claim 29 wherein said tray further defines a second annular ledge within said second chamber proximal said upper surface for engaging said second endcap.

31. An apparatus as defined in claim 30 wherein said second endcap further comprises an o-ring for sealingly engaging said second annular ledge.

32. An apparatus as defined in claim 31 wherein said first closure means comprises a coverslip for engaging said first chamber at said first opening in said tray.

33. An apparatus as defined in claim 22 wherein said bottom plate is coextensive with said tray.

34. A disposable device for growing easily accessible protein crystals of sufficient size and quality to withstand crystal structural analysis using x-ray diffraction techniques, said disposable device comprising:

(a) a tray having an upper and lower surface, said tray defining first and second vertically disposed chambers therein for containing a protein solution and precipitant solution, respectively, said chambers having first and second openings through said upper surface to the exterior of said tray, respectively, and first and second orifices through said lower surface to the exterior of said tray, respectively, said first chamber further having a conically shaped portion adjacent said first orifice;

(b) said tray further defining a channel in said lower surface and in communication with said first and second orifices for containing a predetermined quantity of gelling substance which limits the rate of diffusive mixing of said protein solution and said precipitant solution and substantially reduces solutal convection therein so that said solutions are diffusively mixed over a predetermined period of time defined by said predetermined quantity of gelling substance sufficient to controllably reduce the solubility of said protein solution within said gelling substance to the point of critical supersaturation whereby said protein crystals are grown in said gelling substance in said channel; and (c) closure means detachably connected to said upper surface of said tray for sealingly closing said first and second openings.

35. A disposable device as defined in claim 34 wherein said device further comprises:

(a) sealing means detachably connected to said lower surface of said tray for sealingly engaging said first and second orifices and said channel;

(b) a bottom plate detachably connected to said lower surface of said tray; and (c) an elastomer sheet detachably connected to said lower surface of said tray intermediate said sealing means and said bottom plate.

36. A disposable device as defined in claim 35 wherein the material for said tray is selected from the group consisting of polystyrene, polycarbonate, polysulphone or high molecular weight polyethylene.

37. A disposable device as defined in claim 35 wherein said closure means and said sealing means both comprise a clear synthetic plastic tape.

38. A disposable device as defined in claim 37 wherein the material for said clear synthetic plastic tape is selected from the group consisting of polyester or polypropylene.

39. A disposable device as defined in claim 35 wherein said closure means, said sealing means, said elastomer sheet, and said bottom plate are all coextensive with said tray.

40. A method for growing easily accessible protein crystals in a gel media of sufficient size and quality to withstand crystal structural analysis using x-ray diffraction techniques, said method comprising the steps of:

(a) placing a precipitant solution and a protein solution into separate vertically disposed chambers defined in a housing having upper and lower surfaces;

(b) providing fluid communication between said chambers through a channel defined in said lower surface of said housing; and (c) limiting the rate of diffusive mixing of said solutions through a preselected gelling substance contained in said channel by injecting said gelling substance into said channel prior to placing said precipitant solution and said protein solution into said chambers and allowing said gelling substance to gel, said diffusive mixing occurring over a period of time defined by the quantity of said gelling substance, said period of time sufficient to controllably reduce the solubility of said protein solution to the point of supersaturation whereby protein crystals are grown in said gelling substance in said channel.

* * * * *